United States Patent
Udell

(10) Patent No.: US 7,220,429 B2
(45) Date of Patent: *May 22, 2007

(54) COENZYME Q10 FORMULATION AND PROCESS METHODOLOGY FOR SOFT GEL CAPSULES MANUFACTURING

(75) Inventor: Ronald G. Udell, Beverly Hills, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,396

(22) Filed: Jul. 27, 2005

(65) Prior Publication Data

US 2006/0018958 A1    Jan. 26, 2006

Related U.S. Application Data

(63) Continuation of application No. 10/641,328, filed on Aug. 14, 2003, now Pat. No. 6,955,820.

(51) Int. Cl.
*A01N 25/34* (2006.01)
*A61K 9/48* (2006.01)
*A61K 9/66* (2006.01)

(52) U.S. Cl. .................. 424/451; 424/408; 424/452; 424/455

(58) Field of Classification Search .............. None
See application file for complete search history.

(56) References Cited

U.S. PATENT DOCUMENTS

| | | | |
|---|---|---|---|
| 4,824,669 A | 4/1989 | Folkers et al. | |
| 5,500,416 A | 3/1996 | Miyazawa et al. | |
| 5,645,856 A * | 7/1997 | Lacy et al. | 424/455 |
| 6,020,383 A | 2/2000 | Stone et al. | |
| 6,054,136 A | 4/2000 | Stone et al. | |
| 6,056,971 A * | 5/2000 | Goldman | 424/439 |
| 6,069,167 A | 5/2000 | Sokol | |
| 6,184,255 B1 * | 2/2001 | Mae et al. | 514/720 |
| 6,203,818 B1 | 3/2001 | Vester | |
| 6,300,377 B1 * | 10/2001 | Chopra | 514/715 |
| 6,436,431 B1 * | 8/2002 | Hoffpauer et al. | 424/439 |
| 6,545,184 B1 | 4/2003 | Lipshutz | |
| 6,616,942 B1 | 9/2003 | Udel | |
| 6,623,734 B2 * | 9/2003 | Udell et al. | 424/94.1 |
| 6,664,287 B2 | 12/2003 | Avery et al. | |
| 6,955,820 B1 * | 10/2005 | Udell | 424/451 |
| 7,060,263 B2 * | 6/2006 | Udell et al. | 424/94.1 |
| 2004/0106674 A1 | 6/2004 | Rich et al. | |
| 2005/0069582 A1 * | 3/2005 | Fantuzzi | 424/456 |

FOREIGN PATENT DOCUMENTS

| | | | |
|---|---|---|---|
| JP | 55081813 A | * | 6/1980 |
| JP | 0 888 774 | | 1/1999 |

OTHER PUBLICATIONS

R. Chopra et al., "A New Coenzyme Q10 Preparation with Enhanced Bioavailability," FASEB Journal, 11 (3), p. A586, 1997, Abstract.

M. Weis, et al., "Bioavailability of Four Oral Coenzyme Q10 Formulations in Healthy Volunteers," Molec. Aspects. Med., vol. 15, (Supplement) pp. s273-s280, 1994.

* cited by examiner

*Primary Examiner*—S. Tran
(74) *Attorney, Agent, or Firm*—Dorsey & Whitney LLP; Scott D. Rothenberger

(57) ABSTRACT

A formulation of Coenzyme $Q_{10}$, beta-carotenes, Vitamin E, and medium chain triglycerides in rice bran oil and an optional thickener, such as bee's wax, is provided in a soft gel capsule so that a maximum of the Coenzyme $Q_{10}$ is absorbed by the human body. Generally, about 60 mg of Coenzyme $Q_{10}$ is the normal amount provided daily to a healthy sedentary adult.

38 Claims, No Drawings

COENZYME Q10 FORMULATION AND PROCESS METHODOLOGY FOR SOFT GEL CAPSULES MANUFACTURING

CROSS REFERENCE TO RELATED APPLICATION

This application claims priority of U.S. application Ser. No. 10/641,328, filed on Aug. 14, 2003, now U.S. Pat. No. 6,955,820 which claims priority to U.S. application Ser. No. 09/536,597, filed on Mar. 28, 2000 which claims priority from U.S. Provisional Application Ser. No. 60/126,656, filed Mar. 29, 1999, the contents of which are herein incorporated by reference in their entirety.

BACKGROUND OF THE INVENTION

This invention relates to an improved formulation and process methodology of Coenzyme $Q_{10}$ in producing soft gel capsules of this formulation. Coenzyme $Q_{10}$ ($CoQ_{10}$ or Ubiquinone) is a large molecular weight (863.63 grams) lipid compound that is produced in the liver and perhaps other body organs. The total body content is estimated to be 1.4 to 1.8 grams, depending on the age and the physical fitness of the individual. Although $CoQ_{10}$ is found in the mitochondria and other organelles of every living cell, it appears to be most abundant in tissues with a high number of mitochondria and a high level of metabolic activity. For example, in the metabolically inactive blood there is approximately 4 mg, in the heart, and in the skeletal muscle 1000 mg. The blood acts as a $CoQ_{10}$ reservoir and transport media between endogenous $CoQ_{10}$ synthesis in the liver, exogenous $CoQ_{10}$ absorption from digested food substances in the intestinal tract, and the body cells. Endogenous synthesis appears to be responsible for 56 percent and exogenous sources for 44 percent of the body's $CoQ_{10}$ requirements. These numbers are currently being studied and endogenous $CoQ_{10}$ synthesis may be significantly deficient in the elderly. These deficiencies are not related to the total caloric intake, but rather to the vitamin content of ingested foods. The body requires multiple vitamins for the synthesis of $CoQ_{10}$.

$CoQ_{10}$ requirements of the body are also variable between individuals and are dependent on age, physical activity, and disease. It is estimated that the body $CoQ_{10}$ utilization is between 5 and 9 mg per day. Intercellular $CoQ_{10}$ is required for the synthesis of energy and therefore essential for life. Energy synthesis occurs in the mitochondria, where $CoQ_{10}$ provides an electron for the electron transport chain in the cytochrome system, in which adenosine tripohosphate (ATP) is synthesized. As $CoQ_{10}$ gives up an electron for ATP synthesis, it gets oxidized. If $CoQ_{10}$ is used as an antioxidant, it gets oxidized and is no longer available to provide electrons and function in the synthesis of ATP. Under conditions of high metabolic stress, endogenous sources may become inadequate to meet the body's $CoQ_{10}$ requirement for ATP synthesis. Under such conditions, dietary $CoQ_{10}$ supplementation has been shown to be an effective source. An improved soft gel formulation and process of $CoQ_{10}$ soft gel capsule manufacturing has uses to treat heart failure, chronic fatigue and patients with psoriasis and planter warts. In all cases, it has been found that the improved soft gel formulation at ingestion rates of 30–100 mg/day of $CoQ_{10}$ have been proven to be superior to commercially available 60 mg dry powder capsules, and existing 100 mg/day $CoQ_{10}$ soft gel formulations.

An appropriate $CoQ_{10}$ dosage for a normal individual compared to the dosage necessary for a diseased individual has been difficult to ascertain. Recommended doses of 10 to 30 mg/day were found to be ineffective for patients with significant $CoQ_{10}$ deficiencies. In the past 15 years, it has become generally accepted that poor intestinal absorption of certain $CoQ_{10}$ formulations limits their effective use. For this reason, 50 and 150 mg $CoQ_{10}$ containing tablets or capsules are commercially available to the consumer, at a considerably higher cost.

Folkers et al (U.S. Pat. No. 4,824,669) addresses a soft gel capsule with $CoQ_{10}$ and at least one vegetable oil. This formulation was determined to increase blood $CoQ_{10}$ levels to 2.5 µg/ml compared to 1.6 µg/ml for an equivalent 100 mg dose of dry powder $CoQ_{10}$. Many different $CoQ_{10}$ formulations have appeared which are claimed to increase intestinal absorption. However, intestinal absorption data, collected under near basal conditions, which compare $CoQ_{10}$ alone in oil with dry powder $CoQ_{10}$, are conclusive that oil is a better delivery agent.

SUMMARY OF THE INVENTION

The present invention comprises a stable and nontoxic soft gel Coenzyme $Q_{10}$ formulation and process methodology of Coenzyme $Q_{10}$ for maximum Coenzyme $Q_{10}$ levels in the human body for a given input. A preferred soft gel formulation includes Coenzyme $Q_{10}$ (hereinafter $CoQ_{10}$), Vitamin E, beta-carotene, bee's wax, medium chain triglycerides available as MCT Myglyol S12, and rice bran oil formulated to maximize the body's absorption by maintaining the $CoQ_{10}$ in what may be a supersaturated solution in easily absorbed materials, that can provide healthful effects, as opposed to just fillers. It is important as much of the supplied $CoQ_{10}$ be absorbed, rather than just taking megadoses at frequent intervals as the wholesale cost of $CoQ_{10}$ dry powder in quantity is as much as $2000 per kg. Not only is a relatively large percentage of the $CoQ_{10}$ absorbed, but the volume of the soft gel capsule is minimized, making it easier to swallow and requiring smaller shipping and storage space. Recent studies indicate the preferred soft gel $CoQ_{10}$ formulation should be administered twice a day in dosages of about 30 mg $CoQ_{10}$ in 220 mg capsules, as that amount of $CoQ_{10}$ is about the maximum the body of a healthy sedentary adult can use for maintenance of a preferred blood level. For those who have deficiencies of $CoQ_{10}$, studies have shown that twice a day administration of about 60 mg $CoQ_{10}$ in 435 mg capsules is advantageous. In special instances of $CoQ_{10}$ deficiency, twice a day ingestion of 100 mg $CoQ_{10}$ containing soft gel capsules can be tolerated.

It is therefore an object of the present invention to provide a soft gel formulation of $CoQ_{10}$ and a methodology of formulation processing that produce a significantly greater bioavailability percentage of ingested $CoQ_{10}$ than existing soft or dry formulations.

Another object of the present invention is to provide a soft gel formulation of $CoQ_{10}$ and methodology of administration that produces greater absorption of $CoQ_{10}$ into the intestine.

Another object is to minimize the ingested volume required to maintain a given $CoQ_{10}$ blood content.

Another object is to provide a process that keeps $CoQ_{10}$ in solution in readily absorbed materials, that themselves have beneficial effects.

These and other objects and advantages of the present invention will become apparent to those skilled in the art after considering the following detailed description of the invention.

DETAILED DESCRIPTION OF THE PREFERRED EMBODIMENTS

The unique formulation of the present invention of a stable and non-toxic soft gel Coenzyme $Q_{10}$ where the amount of Coenzyme $Q_{10}$ is balanced with antioxidants and absorption agents to maximize the percentage of Coenzyme $Q_{10}$ in a capsule of a given size, that is delivered to the blood stream from the intestines. The formulation includes: Coenzyme $Q_{10}$, Vitamin E, beta-carotene, bee's wax, medium chain triglycerides (MCT) such as MCT Myglyol S12, and rice bran oil. The preferred soft gel Coenzyme $Q_{10}$ formulation of the present invention is prepared in accordance with the following sequence of ingredients and process.

Rice bran oil, a carrier suspension agent for soft gel formulation useful for absorption of lipophilic ingredients such as Coenzyme $Q_{10}$, is heated to 50 to 60° C. Bee's wax is then added. 50° C. is above the melting point of bee's wax and the wax and oil is mixed until a uniform mixture is formed. Bee's wax thickens the rice bran oil and acts as a suspension agent for subsequent ingredients. Without bee's wax, the other ingredients, which are to suspended inside a transparent gel capsule, might separate or congregate under the effect of gravity, and appear faulty or spoiled to the consumer.

Subsequently, the mixture is cooled to 35 to 45° C. Coenzyme $Q_{10}$, beta-carotenes including alpha and beta carotenes, cryptoxanthin, lutein and zeaxanthin (available commercially as Betatene, available from Cognis Nutrition), Vitamin E, and medium chain triglycerides (MCT) are then simultaneously added to the oil-wax mixture under a vacuum (to eliminate oxidation) and mixed together for one to two hours. beta-carotenes improves the solubility and adds antioxidant value. Vitamin E is an antioxidant preservative that prevents peroxidation of the final product, adds antioxidant value, and is fat soluble. Although Vitamin E is available commercially in 30 IU, 100 IU, 200 IU, 400 IU, and 1000 IU concentrations, for the present invention concentrations from 350 IU to 400 IU are usable, with 372 IU being the preferred concentration, which results in a concentration from 30 to 100 IU in the soft gel capsule. Medium chain triglycerides are fatty acids that improve the lipid environment and enhance absorbibility like the rice bran oil. The bee's wax primarily increases viscosity to keep insoluble components from settling to one side of the soft gel capsule, but it also improves solubility. For instances where viscosity (and in turn gel capsule cosmetics) is not a concern, it can be eliminated.

The resultant mixture is cooled to 25 to 30° C. A nitrogen gas blanket is introduced to shield the mixture for oxygen and the pressure is returned to atmospheric. The mixture is then encapsulated in a soft gel capsule.

| | Ingredient | Amount Range | % in formula |
|---|---|---|---|
| | Formula 1 | | |
| 1. | Vitamin E 372 IU | 0.161 g–2.50 g | 37%–51% |
| 2. | Beta Carotene (20% from D. salina) | 0.00525 g–0.118 g | 1.2%–2.5% |
| 3. | MCT Myglyol 812 | 0.5 g–1.0 g | 12%–21% |
| 4. | Rice Bran Oil | 0.193 g–.50 g | 10%–44% |
| 5. | Yellow Bee's Wax | 0.015 g–.2 g | 1%–4% |
| 6. | $CoQ_{10}$ | 0.5–2.0 g | 10%–15% |
| | Formula 2 | | |
| 1. | Vitamin E 372 IU | 0.161 g–2.50 g | 38.5%–53% |
| 2. | Beta Carotene (20% from D. salina) | 0.00525 g–0.118 g | 1.25%–2.6% |
| 3. | MCT Myglyol 812 | 0.5 g–1.0 g | 12%–22% |
| 4. | Rice Bran Oil | 0.193 g–.50 g | 10%–46% |
| 5. | $CoQ_{10}$ | 0.5–1.0 g | 11%–16% |

The bioavailability or intestinal absorption of $CoQ_{10}$ has been a major controversy in the international $CoQ_{10}$ research community. Previous data indicate that only 1 to 3 percent of dry powder $CoQ_{10}$ formulations are absorbed through the lacteals in the intestines and appear in the blood over a twelve hour interval. In general, blood levels of 1.2 to 1.6 µg/ml have been reported, when taking 30 to 60 mg/day dry powder $CoQ_{10}$ formulation for 30 days. It has been reported that when a dry powder $CoQ_{10}$ formulation is taken with a fat, such as peanut butter, steady-state blood levels of 2.0 to 2.8 µg/ml are measurable.

Multiple clinical trials were conducted in the United States and Europe using the Folkers (U.S. Pat. No. 4,824,669) soft gel. With a dosage of 100 mg/day, multiple investigators have reported group mean blood levels of 2.3 to 3.5 µg/ml depending on the laboratory conducting the measurement.

As observed in recent trials, the bioavailability results found for the present soft gel indicate it provides approximately 50 percent, and with two 30 mg $CoQ_{10}$ containing capsules, 100 percent, of the daily $CoQ_{10}$ requirements of a normal sedentary individual. It would take at least three of the dry powder 30 mg $CoQ_{10}$ capsules to produce the same effects as one soft gel, and six to produce the same effect as two 30 mg $CoQ_{10}$ containing soft gel capsules of the present invention. Regardless of the absorption mechanism, the significantly higher basal blood $CoQ_{10}$ levels (167%) and the 273% greater absorption rate were found in previous studies to establish that the present soft gel formulation is indeed a superior product to dry $CoQ_{10}$ formulations. This may be particularly true for those individuals whose daily $CoQ_{10}$ requirement is elevated due to high physical activity, an increased use of $CoQ_{10}$ as an antioxidant, and disease associated with known $CoQ_{10}$ deficiencies.

Cellular $CoQ_{10}$ content is a function of the number and quality of the cellular mitochondria. For example, the failing heart muscle has 2.2 µg $CoQ_{10}$ per mg of tissue and a blood $CoQ_{10}$ deficiency of 0.3–0.5 g/ml. The normal hearts conditioned heart has 6.3 µg/gm per mg of tissue, and a low basal blood level of 0.5–0.6 µg/ml. These results indicate that supplemental $CoQ_{10}$ enters the cell. This observation has also been reported for skeletal muscles of trained and non-trained athletes.

The subjective and objective responses to supplemental $CoQ_{10}$ in the normal individual appear more rapidly compared to that of the physically unfit or the diseased individual with a $CoQ_{10}$ deficiency. The most probable reason for this observation is that the metabolic machinery (mitochondria) is viable in the non-diseased normal volunteer, whereas the mitochondria are atrophied in the cells of deconditioned and/or diseased individuals. Therefore, it takes time in the diseased individual to build up the mitochondria to a more normal activity level and to normalize their distribution in the organ system involved.

In summary, studies have statistically proven that the present soft gel $CoQ_{10}$ formulation used at 60 mg $CoQ_{10}$/day is superior to dry powder $CoQ_{10}$ formulations, and prior art soft gel formulations.

Thus, there has been shown novel formulations, which fulfill all of the objects and advantages sought therefor. Many changes, alterations, modifications and other uses and applications of the subject invention will become apparent to those skilled in the art after considering the specification. All such changes, alterations and modifications which do not depart from the spirit and scope of the invention are deemed to be covered by the invention which is limited only by the claims that follow.

What is claimed is:

1. A soft gel capsule that encapsulates a coenzyme $Q_{10}$ formulation, wherein the coenzyme $Q_{10}$ formulation comprises:
bee's wax:
coenzyme $Q_{10}$;
beta-carotene;
a medium chain triglyceride;
Vitamin E; and
rice bran oil.

2. The soft gel capsule of claim 1, wherein the coenzyme $Q_{10}$ is present in an amount between 10 percent and 16 percent of the total weight of the formulation.

3. The soft gel capsule of claim 2, wherein the coenzyme $Q_{10}$ is present in an amount between 11 percent and 16 percent of the total weight of the formulation.

4. The soft gel capsule of claim 1, wherein the beta-carotene comprises alpha and beta carotenes, cryptoxanthin, lutein and zeaxanthin.

5. The soft gel capsule of claim 1, wherein the beta-carotene is present in an amount between 1.2 percent and 2.6 percent of the total weight of the formulation.

6. The soft gel capsule of claim 1, wherein the beta-carotene is present in an amount between 1.25 percent and 2.6 percent of the total weight of the formulation.

7. The soft gel capsule of claim 1, wherein the medium chain triglyceride is present in an amount between 12 percent and 22 percent of the total weight of the formulation.

8. The soft gel capsule of claim 1, wherein the medium chain triglyceride is present in an amount between 12 percent and 21 percent of the total weight of the formulation.

9. The soft gel capsule of claim 1, wherein the vitamin E is present in an amount between 37 percent and 53 percent of the total weight of the formulation.

10. The soft gel capsule of claim 1, wherein the vitamin E is present in an amount between 38.5 percent and 53 percent of the total weight of the formulation.

11. The soft gel capsule of claim 1, wherein the rice bran oil is present in an amount between 10 percent and 46 percent of the total weight of the formulation.

12. The soft gel capsule of claim 1, wherein the rice bran oil is present in an amount between 10 percent and 44 percent of the total weight of the formulation.

13. The soft gel capsule of claim 1, wherein the bee's wax is present in an amount between 1 percent and 4 percent of the total weight of the formulation.

14. A soft gel capsule that encapsulates a coenzyme $Q_{10}$ formulation, wherein the coenzyme $Q_{10}$ formulation comprises:
bee's wax:
coenzyme $Q_{10}$;
beta-carotene;
a medium chain triglyceride;
Vitamin E; and
rice bran oil is present in an amount between 10 percent and 46 percent of the total weight of the formulation.

15. The soft gel capsule of claim 14, wherein the coenzyme $Q_{10}$ is present in an amount between 10 percent and 16 percent of the total weight of the formulation.

16. The soft gel capsule of claim 15, wherein the coenzyme $Q_{10}$ is present in an amount between 11 percent and 16 percent of the total weight of the formulation.

17. The soft gel capsule of claim 14, wherein the beta-carotene comprises alpha and beta carotenes, cryptoxanthin, lutein and zeaxanthin.

18. The soft gel capsule of claim 14, wherein the beta-carotene is present in an amount between 1.2 percent and 2.6 percent of the total weight of the formulation.

19. The soft gel capsule of claim 14, wherein the beta-carotene is present in an amount between 1.25 percent and 2.6 percent of the total weight of the formulation.

20. The soft gel capsule of claim 14, wherein the medium chain triglyceride is present in an amount between 12 percent and 22 percent of the total weight of the formulation.

21. The soft gel capsule of claim 14, wherein the medium chain triglyceride is present in an amount between 12 percent and 21 percent of the total weight of the formulation.

22. The soft gel capsule of claim 14, wherein the vitamin E is present in an amount between 37 percent and 53 percent of the total weight of the formulation.

23. The soft gel capsule of claim 14, wherein the vitamin E is present in an amount between 38.5 percent and 53 percent of the total weight of the formulation.

24. The soft gel capsule of claim 14, wherein the rice bran oil is present in an amount between 10 percent and 44 percent of the total weight of the formulation.

25. The soft gel capsule of claim 14, wherein the rice bran oil is present in an amount between 10 percent and 46 percent of the total weight of the formulation.

26. The soft gel capsule of claim 14, wherein the bee's wax is present in an amount between 1 percent and 4 percent of the total weight of the formulation.

27. A soft gel capsule that encapsulates a coenzyme $Q_{10}$ formulation, wherein the coenzyme $Q_{10}$ formulation comprises:
bee's wax:
coenzyme $_{10}$;
beta-carotene;
a medium chain triglyceride;
Vitamin E; and
rice bran oil present in an amount between 10 percent and 44 percent of the total weight of the formulation.

28. The soft gel capsule of claim 27, wherein the coenzyme $Q_{10}$ is present in an amount between 10 percent and 16 percent of the total weight of the formulation.

29. The soft gel capsule of claim 28, wherein the coenzyme $Q_{10}$ is present in an amount between 11 percent and 16 percent of the total weight of the formulation.

30. The soft gel capsule of claim 27, wherein the beta-carotene comprises alpha and beta carotenes, cryptoxanthin, lutein and zeaxanthin.

31. The soft gel capsule of claim 27, wherein the beta-carotene is present in an amount between 1.2 percent and 2.6 percent of the total weight of the formulation.

32. The soft gel capsule of claim 27, wherein the beta-carotene is present in an amount between 1.25 percent and 2.6 percent of the total weight of the formulation.

33. The soft gel capsule of claim 27, wherein the medium chain triglyceride is present in an amount between 12 percent and 22 percent of the total weight of the formulation.

34. The soft gel capsule of claim 27, wherein the medium chain triglyceride is present in an amount between 12 percent and 21 percent of the total weight of the formulation.

35. The soft gel capsule of claim 27, wherein the vitamin E is present in an amount between 37 percent and 53 percent of the total weight of the formulation.

36. The soft gel capsule of claim 27, wherein the vitamin E is present in an amount between 38.5 percent and 53 percent of the total weight of the formulation.

37. The soft gel capsule of claim 27, wherein the rice bran oil is present in an amount between 10 percent and 46 percent of the total weight of the formulation.

38. The soft gel capsule of claim 27, wherein the bee's wax is present in an amount between 1 percent and 4 percent of the total weight of the formulation.

* * * * *

UNITED STATES PATENT AND TRADEMARK OFFICE
CERTIFICATE OF CORRECTION

PATENT NO. : 7,220,429 B2 Page 1 of 1
APPLICATION NO. : 11/190396
DATED : May 22, 2007
INVENTOR(S) : Ronald G. Udell It is certified that error appears in the above-identified patent and that said Letters Patent is hereby corrected as shown below:

On the Title page, in column 1, Item (63) under "Related U.S. Application Data", after "6,955,820", please insert --which is a divisional of Application No. 09/536,597, filed on March 28, 2000, now Pat. No. 6,616,942, which claims benefit of Application No. 60/126,656, filed on March 29, 1999.--

Signed and Sealed this

Tenth Day of July, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,220,429 B2 | Page 1 of 1 |
| APPLICATION NO. | : 11/190396 | |
| DATED | : May 22, 2007 | |
| INVENTOR(S) | : Ronald G. Udell | |

It is certified that error appears in the above-identified patent and that said Letters Patent is hereby corrected as shown below:

TITLE PAGE, Item (56), Under heading FOREIGN PATENT DOCUMENTS, delete "JP   0 888 774  1/1999".

Signed and Sealed this

Thirteenth Day of May, 2008

JON W. DUDAS
*Director of the United States Patent and Trademark Office*